(12) United States Patent
Jung et al.

(10) Patent No.: US 6,802,957 B2
(45) Date of Patent: Oct. 12, 2004

(54) SELF-REFERENCING ENZYME-BASED MICROSENSOR AND METHOD OF USE

(75) Inventors: Sung-Kw n Jung, East Falmouth, MA (US); Richard H. Sanger, Woods Hole, MA (US); Peter J. S. Smith, Falmouth, MA (US); John R. Pepperell, Barrington, RI (US)

(73) Assignee: Marine Biological Laboratory, Woods Hole, MA (US)

( * ) Notice: Subject to any disclaimer, the term of this patent is extended or adjusted under 35 U.S.C. 154(b) by 173 days.

(21) Appl. No.: 09/966,581

(22) Filed: Sep. 28, 2001

(65) Prior Publication Data

US 2004/0173472 A1 Sep. 9, 2004

(51) Int. Cl.⁷ ............................................. G01N 27/327
(52) U.S. Cl. .............................. 205/777.5; 204/403.01; 600/300; 600/376
(58) Field of Search ........................... 204/400, 403.01, 204/403.06, 403.1, 403.11; 205/775, 777.6, 778; 128/898; 600/300, 372, 376

(56) References Cited

U.S. PATENT DOCUMENTS

| | | | |
|---|---|---|---|
| 3,539,455 A | | 11/1970 | Clark, Jr. |
| 5,643,721 A | * | 7/1997 | Spring et al. .................. 435/6 |
| 5,762,770 A | * | 6/1998 | Pritchard et al. ...... 204/403.14 |
| 5,968,340 A | | 10/1999 | Land et al. ................. 205/775 |
| 6,062,225 A | | 5/2000 | Keefe et al. |

OTHER PUBLICATIONS

Guillam, et al., "Glucose Uptake, Utilization, and Signaling in GLUT2–Null Islets" Diabetes, 49:1485–1491 (2000).
Kinlen, et al., "A Mechanistic Investigation of Polyaniline Corrosion Protection Using the Scanning Reference Electrode Technique," Journal of The Electrochemical Society, 146: 3690–3695 (1999).
McDaniel, et al., "Effect of Cytochalasin B on Hexose Transport and Glucose Metabolism in Pancreatic Islets," Diabetologia, 10: 303–308 (1974).
Nuccitelli, "Vibrating Probe Technique for Studies of Ion Transport," Noninvasive Techniqeus in Cell Biology, 273–310 (1990).
Siedleckl, et al., "Atomic force microscopy for characterization of the blomaterial interface," Biomaterials, 19: 441–454 (1998).
Wipf, et al., "Scanning Electrochemical Microscopy. 15. Improvements in Imaging via Tip–Position Modulation and Lock–in Detection," Anal. Chem., 64: 1362–1367 (1992).
Wree, "Principles of the 2–deoxyglucose Method for the Determination of the Local Cerebral Glucose Utilization," European Journal of Morphology, 28:132–138 (1990).

(List continued on next page.)

*Primary Examiner*—Kaj K. Olsen
(74) *Attorney, Agent, or Firm*—Wilmer Cutler Pickering Hale and Dorr LLP (57) ABSTRACT

A micron-scale self-referencing microsensor is disclosed which uses an enzyme-based electrode to measure the flux of an electrochemically inactive analyte such as glucose. The electrode oscillates between at least two positions. In the presence of the analyte, the enzyme generates a species detectable by the electrode.

16 Claims, 8 Drawing Sheets

OTHER PUBLICATIONS

Zhang, et al., "In vitro and in vivo evaluation of oxygen effects on a glucose oxidase based implantable glucose sansor," Analytica Chimica Acta, 281: 513–520 (1993).

Abstract—Presentation at the American Society of Reproductive Medicine, Oct., 2000, San Diego, California, US.

Danuser, "Computer Vision Controlled Near–Field Positioning of Microscopic Probes," Bull. Swiss Soc. Micrs–Technique, 22: 34–39 (1998).

Smith, Peter J.S. et al., "Self–Referencing, Non–Invasive, Ion Selective Electrode for Single Cell Detection of Trans–Plasma Membrane Calcium Flux," Microscopy Research and Technique, 46: 398–417 (1999).

Land et al., "The Self–Referencing Oxygen–Selective Microelectrode: Detection of Transmembrane Oxygen Flux From Single Cells," Journal of Experimental Biology, 202:211–218 (1999).

Kumar et al., "Nerve Injury Induces a Rapid Efflux of Nitric Oxide (NO) Detected with a Novel NO Microsensor," Journal of Neuroscience, 21(1): 215–220, (2001).

Hu et al., "Rapid Changes in Local Extracellular Rat Brain Glucose Observed with an in Vivo Glucose Sensor," Journal of Neurochemistry, 68:1745–1752, (1997).

Smith, Peter J.S. et al., "Noninvasive Measurement of Hydrogen and Potassium Ion Flux from Single Cells and Epithelial Structures," Am. J. Physiol. Cell Physiol., 280: C1–C11 (2001).

Santerre et al., "Insulin Synthesis in a Clonal Cell Line of Simian Virus 40–transformed Hamster Pancreatic Beta Cells," Proc. Natl. Acad. Sci., 78:7: 4339–4343 (1981).

Jung et al., "Oxygen Microsensor and its Application to Single Cells and Mouse Pancreatic Islets," Anal. Chem. 71: 3642–3649, (1999).

Jung et al., Correlated Oscillations in Glucose Consumption, Oxygen Consumption, and Intracellular Free Ca2 in Single Islets of Langerhans.

Jung et al., "Development and Application of a Self–Referencing Gluocose Microsensor . . . ," Anal. Chem. 73: 3759–3767, (2001).

\* cited by examiner

SELF-REFERENCING ENZYME-BASED MICROSENSOR AND METHOD OF USE

STATEMENT OF GOVERNMENT RIGHTS

This invention was made with government funding under grant no. P41 RR01395 from the National Institutes of Health. The government may have certain rights in this invention.

BACKGROUND OF THE INVENTION

1. Field of the Invention

This invention relates to biochemical sensors for use in detecting analytes. In particular, the invention relates to self-referencing enzyme-based microsensors for measuring the flux of electrochemically inactive analytes.

2. Description of the Related Art

Glucose transport is a common and important component of cell metabolism. Studying glucose transport in pancreatic β-cells is particularly interesting, because these cells play a role in insulin secretion and Type II diabetes. In pancreatic β-cells, the movement of glucose from the blood across the plasma membrane is a key component in controlling insulin secretion, the chemical regulator of blood glucose concentration. Thus, following the glucose transport process in pancreatic β-cells can provide important insights into the mechanisms underlying insulin secretion and Type II diabetes. Central to the control of insulin secretion is the concept of a cellular glucose sensor and its regulatory role. Further, down-regulation of the glucose transporter in pancreatic β-cells correlates with decreased glucose uptake and the loss of insulin secretion in Type II diabetes. In order to gain further understanding of glucose transport, insulin secretion, and Type II diabetes, it would be desirable to measure changes in the glucose microenvironment surrounding pancreatic β-cells non-invasively and in real time.

Despite a strong interest in tracking glucose transport and consumption, there has been no method available for the real-time measurement of glucose flux. Glucose consumption has been measured using, for example, the radiochemistry of $^3H_2O$ production from D-[5-$^3H$] glucose metabolism (Guillam et al., *Diabetes* 49:1485–1491 (2000)), $^{14}CO_2$ production from [$^{14}C$] glucose oxidation (McDaniel et al., *Diabetologia* 10:303–308 (1974)), or microfluorometry of glucose and 2-deoxyglucose uptake using a cocktail of hexokinase, ATP, glucose-6-phosphate and NADP (Wree, *Eur. J. Morhphol.* 28:132–138 (1990)). Such techniques employing radiochemistry are hazardous and time consuming, and cannot be used with living tissues to provide real-time flux measurements.

Glucose and many other biologically important molecules such as, for example, lactate and glutamate, are not electrochemically active. Such molecules do not readily undergo reaction at an electrode to produce a detectable current, and therefore they cannot directly be measured electrochemically. However, many such molecules are acted upon by enzymes to generate electrochemically active species that are detectable by an electrode. For example, the processing of glucose by the enzyme glucose oxidase (GOx) generates hydrogen peroxide, which is easily detectable electrochemically. The process, which requires oxygen as a co-substrate, is outlined in Equations (1) and (2). Similar transformations are performed on lactate and glutamate by lactate oxidase and glutamate oxidase, respectively.

$$glucose + O_2 \xrightarrow{GOx} gluconolactone + H_2O_2 \quad (1)$$

The production of $H_2O_2$ is measured at a charged platinum electrode surface:

$$H_2O_2 \xrightarrow{+600mV} O_2 + 2H^+ + 2e^- \quad (2)$$

Enzyme-based electrodes for indirectly detecting biologically important yet electrochemically inactive molecules such as glucose are well known in the art (e.g., U.S. Pat. No. 3,539,455). Glucose oxidase-based electrodes have been used to detect in vivo levels of circulating glucose (Hu et al., *J. Neurochem.* 68:1745–1752 (1997); Zhang et al., *Anal. Chim. Acta*, 281:513–520 (1993)), although in such applications the electrode is usually greater than 200 μm in tip diameter. Miniaturized glucose microsensors are disclosed by Jung et al., *J. Biol. Chem.* 275:6642–6650 (2000). However, a need exists in the art for an enzyme-based electrode technique for non-invasively and accurately measuring the real-time flux of glucose and other electrochemically inactive analytes in a biological microenvironment.

Position modulation of microprobes has been used to enhance detection in various applications such as scanning electrochemical microscopy (Wipf et al., *Anal. Chem.* 64:1362–1367 (1992)), atomic force microscopy (Siedlecki et al., *Biomaterials* 19:441–454 (1998)), and scanning reference electrode techniques used in both biological and materials sciences (Nuccitelli, "Vibrating Probe Technique for Studies of Ion Transport," in *Noninvasive Techniques in Cell Biology*, pp. 273–310, Foskett et al. eds., Wiley-Liss, Inc., 1990; Kinlen et al., *J. Electrochem. Soc.* 146:3690–3695 (1999)). Position modulation enhances detection by self-referencing electrodes, which measure difference values between two positions, thereby reducing the impact of noise and drift, which are common to both positions. Self-referencing sensors have been used to measure the flux of ions (U.S. Pat. No. 6,062,225; Smith et al., *Microsc. Res. Tech.* 46:398–417 (1999); Smith et al., *Am. J. Physiol.* 280:C1–C11(2001)), as well as gases such as oxygen and nitric oxide (U.S. Pat. No. 5,968,340; Kumar et al., *J. Neurosci.* 21:215–220 (2001); Land et al., *J. Exp. Biol.* 202: 211–218 (1999)) in biological microenvironments.

SUMMARY OF THE INVENTION

The present invention depends, in part, upon the development of an enzyme-based microsensor capable of operating in self-referencing mode on a micron-scale to measure the real-time flux of an electrochemically inactive analyte in a biological microenvironment non-invasively and with reduced impact of sensor drift or noise. Fluxes on the order of pmol cm$^{-2}$ s$^{-1}$ can be measured using the methods and systems of the invention. For example, glucose fluxes as low as about 8 pmol cm$^{-2}$ s$^{-1}$ and glutamate fluxes as low as about 5 pmol cm$^{-2}$ s$^{-1}$ have been measured using self-referencing enzyme-based microsensors of the invention.

In one aspect, the invention provides a system for determining a flux of an analyte with respect to a source. The system comprises an electrode that includes an enzyme specific for the analyte. In the presence of the analyte, the enzyme generates a species detectable by the electrode. The system also comprises a translational mechanism for moving the electrode between at least two positions. At each of the positions, the concentration of the detectable species is dependent on the concentration of the analyte. The system can also comprise a voltage source for applying a voltage to a portion of the electrode at each of the two positions. Upon application of the voltage, the detectable species undergoes a chemical change to generate a position-dependent current. The system can also comprise sensing circuitry for detecting a current from the electrode in response to the applied voltage at each position. The system can also comprise analysis circuitry for converting the detected currents into a determination of flux of the analyte. The analysis circuitry can comprise a computer. The system can also comprise a controller for providing to the translational mechanism a frequency for the motion of the electrode. The controller can comprise a computer. The system can also comprise an oxygen source for preventing distortion of the flux determination by oxygen depletion.

In some embodiments, the source comprises a mammalian cell. In some embodiments, the enzyme is a dehydrogenase. In other embodiments, the enzyme is an oxidase. For example, the analyte and enzyme can be glucose and glucose oxidase, glutamate and glutamate oxidase, or lactate and lactate oxidase, respectively. In some embodiments, the detectable species is hydrogen peroxide.

In another aspect, the invention provides a system for determining a flux of each of a plurality of analytes with respect to a source. For each analyte, the system comprises an electrode including an enzyme specific for that analyte. In the presence of each analyte, the corresponding enzyme generates a species detectable by the electrode. The system also comprises a translational mechanism for moving each of the electrodes between at least two positions. At each of the positions, the concentration of the detectable species is dependent on the concentration of the analyte. The system can also comprise a voltage source for applying a voltage to a portion of each of the electrodes at each of the two positions. Upon application of the voltage, each of the detectable species undergoes a chemical change to generate a position-dependent current. The system can also comprise sensing circuitry for detecting a current from each of the electrodes in response to the applied voltage at each position. The system can also comprise analysis circuitry for converting the detected currents to a determination of flux for each of the analytes.

In another aspect, the invention provides a method of determining a flux of an analyte with respect to a source. The method comprises oscillating an electrode including an enzyme between first and second positions proximal to the source. The enzyme contacts the analyte and generates a species detectable by the electrode. At each of the positions, the concentration of the detectable species is dependent on the concentration of the analyte. A voltage is applied to a portion of the electrode so that the detectable species undergoes a chemical change to generate a position-dependent current. The current is sensed at the first and second positions and the sensed currents are used to determine the flux of the analyte with respect to the source. The method can also comprise providing oxygen to the source to prevent distortion of the flux determination by oxygen depletion.

In some embodiments, the source comprises a mammalian cell. In some embodiments, the enzyme is a dehydrogenase. In other embodiments, the enzyme is an oxidase. For example, the enzyme and analyte can be glucose oxidase and glucose, glutamate oxidase and glutamate, or lactate oxidase and lactate, respectively. In some embodiments, the detectable species is hydrogen peroxide. In such embodiments, the method can also comprise contacting the source with catalase to prevent distortion of the flux determination near the source.

In some embodiments, the oscillating step includes moving the electrode at a frequency in the range of about 0.1 Hz to about 0.3 Hz. In some embodiments, the distance between the first and second positions is between about 10 $\mu$m and about 50 $\mu$m. In some embodiments, the first and second positions lie within a gradient of the analyte with respect to the source. In some embodiments, the distance between the surface of the source and the midpoint between the first and second positions is between about 2 $\mu$m and about 500 $\mu$m.

In another aspect, the invention provides a method of assessing the viability of an embryo by determining a flux of an analyte with respect to the embryo. The method comprises oscillating an electrode including an enzyme between first and second positions proximal to the embryo. The enzyme contacts the analyte and generates aspecies detectable by the electrode. At each of the positions, the concentration of the detectable species is dependent on the concentration of the analyte. A voltage is applied to a portion of the electrode so that the detectable species undergoes a chemical change to generate a position-dependent current. The current is sensed at the first and second positions. The sensed currents are used to determine the flux of the analyte with respect to the embryo, and the flux determination is used to assess the viability of the embryo.

In still another aspect, the invention provides a method of screening for compounds that affect a transmembrane flux of an analyte with respect to a cell. The method comprises oscillating an electrode including an enzyme between first and second positions proximal to the cell. The enzyme contacts the analyte and generates a species detectable by the electrode. At each of the positions, the concentration of the detectable species is dependent on the concentration of the analyte. A voltage is applied to a portion of the electrode so that the detectable species undergoes a chemical change to generate a position-dependent current. The current is sensed at the first and second positions and the sensed currents are used to determine the transmembrane flux of the analyte with respect to the cell. The cell is then contacted with a test compound. The oscillating, voltage application, current sensing, and flux determination steps are repeated for the cell in the presence of the test compound. The transmembrane flux of the analyte with respect to the cell in the presence of the test compound is compared to the transmembrane flux of the analyte with respect to the cell in the absence of the test compound. A difference in flux values indicates that the test compound affects the transmembrane flux of the analyte with respect to the cell.

DETAILED DESCRIPTION OF THE INVENTION

I. Self-Referencing System

Figure 1A:
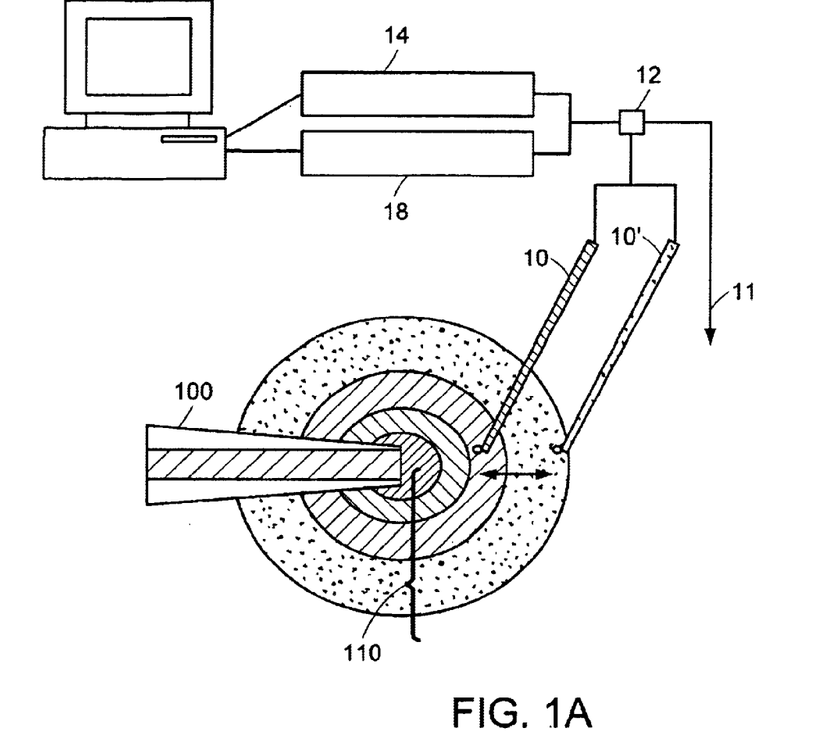
FIG. 1A is a schematic diagram of a self-referencing system of the present invention.

Referring to FIG. 1A, the self-referencing enzyme-based microsensor system of the invention comprises an electrode 10 for measuring the flux of an analyte with respect to a source. The term "analyte," as used herein, refers to a molecule to be detected or measured. Preferred analytes for detection by self-referencing enzyme-based microsensors of the invention include any analyte that is electrochemically inactive, i.e., does not readily undergo reaction at an electrode to produce a detectable current, but is acted upon by an enzyme to generate a species that is detectable by an electrode. Examples of such analytes include, but are not limited to, biologically significant molecules such as glucose, lactate, and glutamate. The term "flux," as used herein, means the number of analyte molecules crossing a unit area per unit time (see Equation (3) below). The methods and systems of the present invention allow for the non-invasive measurement of flux with a sensitivity on the order of $pmol/cm^2/s$.

The electrode 10 oscillates between and takes measurements at two positions, which represent near and far poles of translation with respect to the source. In FIG. 1, the electrode 10 is designated 10 at the near pole of translation and 10' at the far pole of translation. Preferably, both poles of translation lie within a gradient of the analyte with respect to the source. The term "gradient," as used herein, refers to a region in which there is a variation in concentration of an analyte over distance. The oscillation of electrode 10 is effected by a head stage 12 driven by a step motor controller 14. The head stage 12 is also connected to a reference ground electrode 11. A computer 16 controls the frequency of sensor translation. The computer 16 can use software such as IonView (BioCurrents Research Center (BRC), Marine Biological Laboratory (MBL), Woods Hole, Mass.) to report current changes as the sensor moves in a gradient. The current measurements of the electrode 10 are amplified by a preamplifier within the head stage 12 and by a current amplifier 18. The electrode 10 is positioned proximal to an analyte source 100 which produces a gradient 110 of the analyte. The analyte source 100 is shown as a pipette tip but is typically a cell in actual use.

The experimental platform can be constructed around an inverted microscope such as an Axiovert 10 (Carl Zeiss Inc., Oberkochen, Germany) fitted with a stage plate upon which the translational motion control system, carrying the head stage amplifier and sensor, is mounted. Such an arrangement is disclosed by Smith et al., *Microsc. Res. Tech.* 46:398–417 (1999), the teachings of which are incorporated herein by reference. The motion control system can include translation stages such as Newport 310 (Newport Corp., Irvine, Calif.) arranged in an orthogonal array and driven by stepper motors, for example size 17 (Oriental Motor, Japan), whose movements are controlled by software such as IonView. Such an arrangement provides nanometer resolution of movement of the head stage along with the glucose sensor in either a square wave oscillation or single-step mode, as described by Danuser, *Bulletin Swiss Soc. Micro-Technique, Lausanne* 22:34–39 (1998), the teachings of which are incorporated herein by reference. The sensor positioning relative to a biological target can be observed with bright field optics and guided remotely by viewing with a video camera such as Burle TC655EAC (Burle Industries, Inc., Lancaster, Pa.). The entire assembly can be mounted on an anti-vibration table (Technical Manufacturing Corp., Peabody, Mass.) and housed within a thermally insulated Faraday box maintained at 37° C. with a temperature control system. Data then can be collected, for example using IonView at 1000 Hz or Axoscope (Axon Instruments, Foster City, Calif.) at 300 Hz with a low pass cutoff frequency of 10 Hz. Motion controllers, temperature controllers, and amplifiers, as well as coordinating software, for use in the present invention are produced by the BioCurrents Research Center (Marine Biological Laboratory, Woods Hole, Mass.).

Figure 1B:
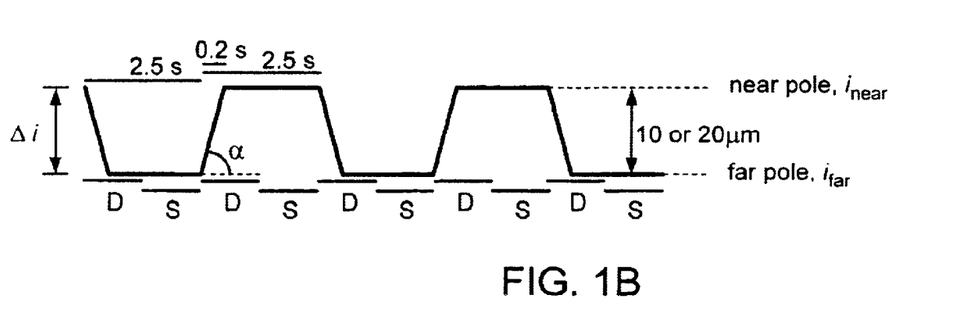
FIG. 1B is a plot of current differential versus time.

FIG. 1B is a graph showing the movement of the electrode 10, which approximates a square wave. The speed of sensor translation can be adjusted by using the computer 16 with software such as IonView to regulate the length of the step as well as the angle $\alpha$. The frequency of sensor translation is selected based on sensor characteristics and the relaxation time of the medium, i.e., the time required to recover from disturbances caused by probe movement. Operable self-referencing frequencies can be up to about 5 Hz. Preferred frequency ranges are compound-specific and dependent on sensor efficiency and boundary conditions. In the case of glucose measurement with glucose oxidase, the preferred frequency range is from about 0.1 Hz to about 0.3 Hz. This can be somewhat slower than the frequency used for self-referencing probes measuring the flux of ions or gases due to the slower reaction and longer time required for relaxation of the medium in the case of glucose. The operable and preferred frequencies for other enzyme-based applications can be similar to those used for glucose. The present invention has been used to measure glucose flux surrounding small aggregates of a cultured cell line comprising pancreatic β-cells derived from the hamster insulinoma tumor (HIT). For such applications, a square-wave translational frequency of 0.2 Hz is preferred. In FIG. 1B, the frequency of translation was set at 0.2 Hz.

Current values measured by the electrode 10 are sent to the computer 16 and processed by software such as IonView. The software preferably discards the first half of the values (labeled D in FIG. 1B) at each position to minimize artifacts from sensor motion and errors caused by response time limitations and the period of gradient reestablishment after translation. The software then samples the second half of the values (labeled S in FIG. 1B) at each position for mathematical subtraction. The software reports both total current (i) and differential current ($\Delta i$). Total current (i), which is used to calibrate the sensor, includes the background signal caused by analyte concentration in the bulk as well as fluctuations within the system, particularly between the sensor and the return electrode. Total current (i), therefore, represents the sum of all sources, bulk analyte concentration, drift, and biological flux. Differential current (Δi) is defined as $(i_{near} - i_{far})$, where $i_{near}$ is the current at the translational position/pole nearest the source and $i_{far}$ is the current at translational position/pole farthest from the source. The term "self-referencing" arises from the procedure of comparing the signal between sensor and ground at each pole of translation and calculating the differential (Δi), thereby removing the comparatively large background signal and drift that are common to both poles of translation. This procedure allows the selective amplification of the differential signal, and thus greatly enhances detection in comparison with stationary sensors.

Amplification is the critical function of the electronics associated with the self-referencing biosensor. Such amplification allows for resolution of extremely small differential current values (femtoAmp) extracted from the larger (milliAmp) total current values measured at the poles of translation. Small differential signals, once extracted from background and drift, are amplified to take full advantage of the dynamic range (±10V) of an analog-to-digital converter (ADC). Data acquisition can be performed by, for example, a Data Translation DT3005 (Data Translation, Marlboro, Mass.), a 16 bit board providing a voltage resolution of 305 μV per bit. The head stage amplifier contains a current-to-voltage converter whose conversion factor is dependent upon the chosen resistor and can be, for example, 1 volt per nA.

To discriminate small differential signals from larger background and drift values, a higher resolution data acquisition system can be used. For example, a 24-bit ADC theoretically can resolve 1.2 μV with a dynamic range of ±10V without amplifying probe output. Signal extraction is then performed using computational methods. Alternatively, background and drift can be offset by adding a reference voltage to probe output before gain is applied. Thus, small differential signals are brought within the dynamic range even after amplification. The reference or offset voltage can be generated by a potentiometer adjusted to set the offset voltage to the appropriate level. Alternatively, a high pass filter can be set to filter out voltage changes slower than the differential signals generated by moving the probe in self-referencing mode. Thus, the high pass filter effectively blocks the non-changing portion of the probe output. The output of a low pass filter can be used as the offset voltage. This effectively sets up a high pass filter, subtracting or nulling voltages changing more slowly then the low pass frequency. Faster signals then go on to be amplified. This method eliminates voltage errors due to capacitor leakage in traditional high pass filters. Another alternative method for generating a reference voltage involves integrating probe output for several seconds to generate an average value using the above-described low pass filter. The computer can then briefly close an analog switch to transfer the integrated value into a sample and hold amplifier (SHA). The value stored in the SHA is then used as the offset voltage. This method is less frequency-dependent than filtering methods. Alternatively, a reference voltage can be generated using computer nulling, whereby the computer digitizes the output at low gain to determine the probe's static voltage and then sets the digital to analog converter to the appropriate level for use as the offset voltage.

II. Electrodes

A self-referencing sensor of the invention must respond reasonably rapidly to new analyte concentrations, as the sensor resides at each measurement position for only a short period of time. Further, the mechanism of detecting analytes using oxidase enzymes involves oxygen (see, e.g., Equations (1) and (2)), and oxygen consumption frequently accompanies consumption of analytes of interest by cells. Therefore, the oxygen concentration surrounding the cells may be changing as analyte flux measurements are taken, such that oxygen dependence of the sensor can interfere with analyte flux measurements according to the invention. Considering these limitations, a preferred design for a glucose oxidase electrode of the invention is that shown in FIG. 2, which affords acceptable oxygen dependence as well as fast response time. Such an electrode is disclosed by Jung et al., *J. Biol. Chem.* 275:6642–6650 (2000), the teachings of which are incorporated herein by reference. Alternative electrodes of the invention can be constructed according to the same design by replacing glucose oxidase with another redox enzyme. The term "redox enzyme," as used herein, refers to an oxidoreductase, i.e., an enzyme that catalyzes an oxidation-reduction reaction involving an analyte of the invention. The redox enzyme included in the electrode of the invention acts on an analyte of interest to generate a species detectable by the electrode. The concentration of the detectable species generated is proportional to the concentration of the analyte. For example, glucose oxidase generates the electrochemically detectable species hydrogen peroxide at a concentration proportional to the concentration of glucose present, as shown in Equation (1).

Figure 2:
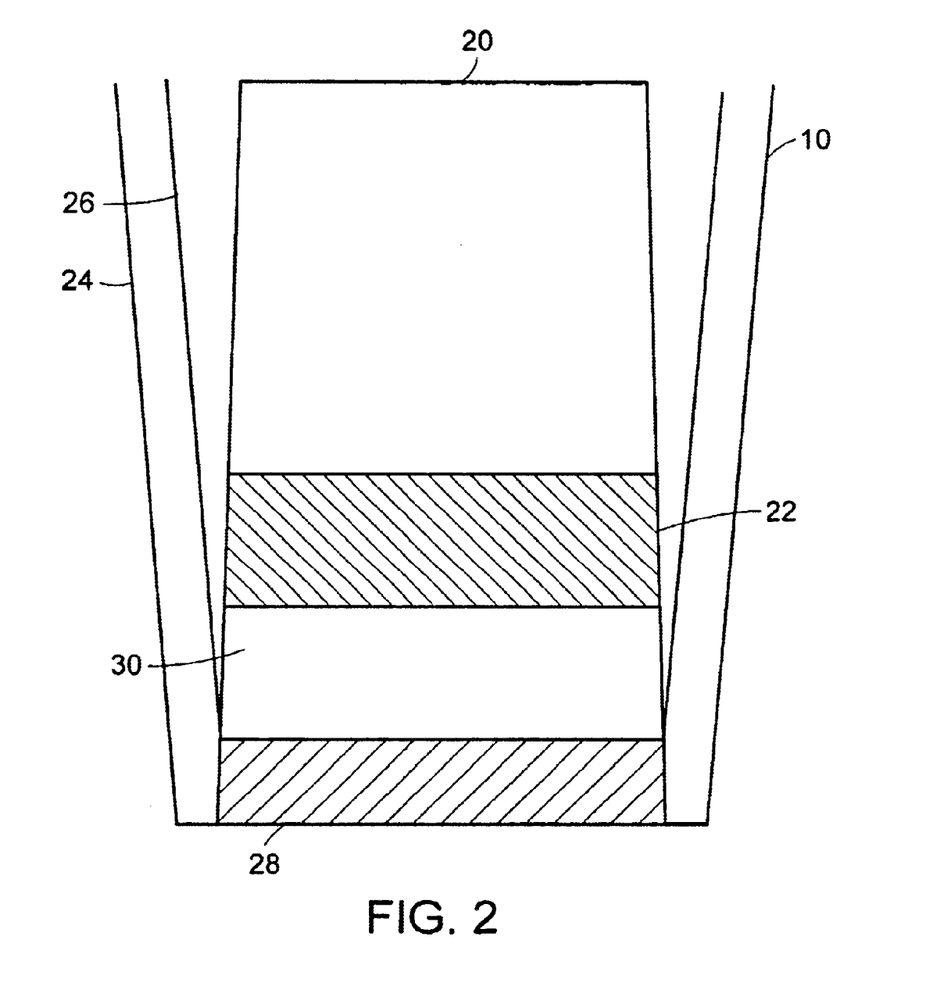
FIG. 2 is a cross-sectional view of the tip of a glucose microsensor of the invention.

FIG. 2 illustrates the construction of such a glucose microsensor. The tip of the electrode 10 has a diameter of about 7 μm. The diameter of the tip of an electrode 10 of the invention can range from about 5 μm to over 50 μm, and preferably can be between about 5 μm and about 7 μm. However, the preferred tip diameter will vary according to the application, and larger sensors can be used with tissues and multiwell plates where spatial resolution is less critical. The electrode 10 includes a platinum (Pt) wire 20 capped with a layer of platinum black 22 secured in a pulled glass capillary 24 with a UV curable optical adhesive 26 such as, for example, Norland Optical Adhesive 81 (Norland Products Inc., New Brunswick, N.J.). The electrode 10 is tipped with a cellulose acetate membrane 28. Suitable alternative materials for the membrane 28 include Nation (DuPont, Wilmington, Del.) and polyurethane. Between the lower end of the platinum wire 20 and the membrane 28 is a layer of glucose oxidase 30 such as EC 1.1.3.4., type X-S from *Aspergillus niger* (Sigma, St. Louis, Mo.).

Alternatively, a carbon fiber electrode enclosed in a glass microcapillary can be used. The fiber is electrochemically and chemically treated to enable the attachment of biotin molecules, to which avidin is subsequently bound. Biotinylated enzyme such as, for example, glucose oxidase, is then bound to the avidin. Further alternative methods for enzyme immobilization use chemicals with bifunctional or multifunctional groups to link enzyme molecules to the electrode surface. For example, 3-mercaptopropyltrimethoxysilane or 3-maleimodopropionic acid or (4-aminobutyl) dimethylmethoxysilane can be employed as a covalent linker (see Jung et al., *Anal. Chem.* 68:591–596 (1996); Hendji et al., *Sens. Actuators B* 15–16:127–134 (1993)). Alternatively, enzyme molecules can be entrapped into the lattices of a semi-permeable gel or enclosed in a semi-permeable polymer membrane (see Gill et al., *Ann. N.Y. Acad. Sci.* 799:697–700 (1996); Tian et al., *Anal. Chim. Acta* 443:9–16 (2001)).

The reference electrode 11 is preferably made of Ag/AgCl.

III. Flux Determinations

The differential current Δi derived from the electrode measurements can be converted into a concentration difference (ΔC), which can be converted into a flux measurement according to the 1st Fick equation:

$$J = -D_G (\Delta C/\Delta r) \quad (3)$$

where J is flux in mol cm$^{-2}$ s$^{-1}$, $D_G$ is the diffusion coefficient of the analyte (e.g., 6.7×10$^{-6}$ cm$^2$ s$^{-1}$ for glucose) and (ΔC/Δr) is the concentration difference over the distance of electrode translation (Δr). In practice, flux values calculated from measurements taken by a self-referencing electrode are generally smaller than flux values calculated from corresponding measurements taken by a stationary electrode, particularly near a source (see FIG. 3B). This disparity reflects a frequency-dependent underestimate of Δi by the self-referencing electrode and likely results from limitations on reestablishing the full gradient after sensor movement, which causes local mixing. The disparity can be compensated for by replacing ΔC in Equation (3) with ($C_f$Δi)/S, such that flux measured by a self-referencing electrode can be calculated as follows:

$$J = -D_G \frac{C_f \Delta i}{S \Delta r} \quad (4)$$

where $C_f$ is a compensation factor, S is the sensitivity of the glucose sensor in pA/mM, and other notations are the same as in Equation (3). As shown in Table 1, lower frequencies of electrode translation correspond to smaller $C_f$ values, i.e., the glucose signal more closely approximates the full response as the sensor stays longer in each position. However, limitations caused by the frequency of translation must be balanced against the increased impact of drift caused by remaining at one measurement position too long, which is especially problematic for shallower gradients. Due to drift and noise, stationary electrodes have difficulty measuring flux values smaller than 1 nmol cm$^{-2}$ s$^{-1}$. In contrast, self-referencing electrodes of the present invention have been demonstrated to reliably measure fluxes as low as 8.2±0.4 pmol cm$^{-2}$ s$^{-1}$.

TABLE 1

Effect of Self-Referencing Frequency on Compensation Factor ($C_f$)[1]

| Self-Referencing Frequency (Hz) | Compensation Factor ($C_f$) |
|---|---|
| 0.10 | 1.20 ± 0.04 (n = 5)[2] |
| 0.15 | 1.32 ± 0.03 (n = 5)[2] |
| 0.20 | 1.46 ± 0.09 (n = 6)[2] |
| 0.30 | 1.51 ± 0.16 (n = 5)[2] |

[1]$C_f$ was obtained by comparing the difference values between two positions measured in stationary mode with those measured in self-referencing mode.
[2]Values are expressed as mean ± SEM with the number of sensors tested (n).

Signal averaging can be used in the analysis of Δi to further improve signal quality by reducing the impact of noise and transient drift, which is minimized by the self-referencing technique. However, problems may arise from changes in electrode sensitivity over the recording period. The flux calculation in Equation (4) is, valid under the condition that the sensor sensitivity (S) remains constant during measurement. Constant monitoring of the total (i) and difference (Δi) currents, as done by IonView, allows for the incorporation of time-dependent sensitivity changes. Alternatively, a rejection criterion can be used, such that data are rejected if sensor drift exceeds a given level, for example ±5% over the experimental period.

The full translational distance, i.e., both poles of translation, should lie within the analyte gradient surrounding a source to allow for accurate flux determinations. Operable translational distances range from about 0.1 µm to about 3 cm, with preferred translational distances ranging from about 10 µm to about 50 µm, most preferably from about 10 µm to about 30 µm. To assure that both poles of translation lie within the analyte gradient surrounding a source, flux measurements must be taken proximal to the source. One of skill in the art will understand that the acceptable proximity for taking flux measurements will vary with the size of the source, the analyte concentration and the strength of the gradient. However, distances qualifying as "proximal to" the source in a biological microenvironment generally can be up to about 1000 µm from the surface of the source. Those of skill in the art will understand that preferred distance ranges will vary with the geometry of the source and can be determined on a case-by-case basis. Although proximity to the source is required, the flux calculations of Equations (3) and (4) assume that the sensor is sufficiently far from the source to allow free diffusion to and from the surface. Limitations on analyte diffusion can cause artificial buildup or depletion of analyte below the electrode surface, which can distort analyte flux measurements taken too close to a source. An advantage of the self-referencing probe of the invention is that, unlike stationary electrodes, it is sensitive enough to accurately measure flux at distances far enough from the source to avoid such boundary artifacts. Average distances from the surface of the source for taking flux measurements can range from about 2 µm to about 500 µm, with preferred distances ranging from about 10 µm to about 80 µm, most preferably from about 60 µm to about 80 µm. The ratio of the preferred distance to the surface compared to the modulation distance for the experiments described herein is about 3.5, which satisfies the criteria proposed for scanning electrochemical microscopy by Wipf et al., Anal. Chem. 64:1362–1367 (1992). In general, the ratio of the distance to the surface compared to the modulation distance can be between about 1 and about 5, preferably between about 2.5 and about 3.5.

The flux calculations of Equations (3) and (4) assume that the gradient between two measured points is relatively linear. Experimental evidence suggests that this assumption is reasonable under the conditions contemplated in the present invention. For example, ion fluxes from mouse zygotes demonstrate a diffusion-based decline defined as 1/r$^2$, where r is measured from the center of the cell, as reported by Trimarchi et al., Biol. Reprod. 63:851–857 (2000). When flux measurements are taken at a mean distance of between about 100 µm and about 250 µm from the center of a cell cluster with a radius of between about 35 µm and about 150 µm, the error in assuming linearity should be negligible. As long as the measurements are performed at least about 85 µm from the cell cluster, linearity can be safely assumed.

Assuming that analyte flux is evenly distributed over the exposed surface of a cell cluster, a reasonable assumption for clusters grown from one cell, approximate analyte consumption for an entire cluster can be calculated and compared to values available in the literature. Pancreatic β-cells in culture attempt to form islets, rounding up as spheroids. This allows for an estimation of cluster volume by assuming a shape equivalent to an oblate spheroid, where the lateral radius is symmetrical ($R_1$) and larger than the vertical radius ($R_2$). $R_2$ can be estimated by using the motion controller to bring a probe touching the cluster surface to the coverslip. $R_2$ has been found to be approximately 0.8$R_1$. In the following calculations the portion of the spheroid resting on the coverslip is not compensated for. The cluster volume (V) is calculated as follows:

$$V = 4/3[\Pi \cdot (R_1^2 \cdot R_2)] \quad (5)$$

As flux values are measured during self-referencing between x and $(x+\Delta r)$ μm, where x is the distance from the cluster surface, the apparent surface area (SA) will be:

$$SA = 4\Pi[(2R_1+R_2)/3+x+\Delta r/2]^2 \quad (6)$$

Flux multiplied by the surface area at the collection point gives a measure of consumption, which can be related to the volume of the cluster. As described in Example 3 below, applying Equations (5) and (6) to measurements made according to the methods of the invention rendered a glucose consumption per unit volume of 61.7 fmol nl$^{-1}$ s$^{-1}$ for pancreatic β-cell clusters, which comports with the glucose consumption value of ~48 fmol nl$^{-1}$ s$^{-1}$ reported by Freyer et al., *J. Cell. Physiol.* 124:516–524 (1985) for mouse tumor cell clusters.

IV. Obstacles to Implementation

Figure 4A:
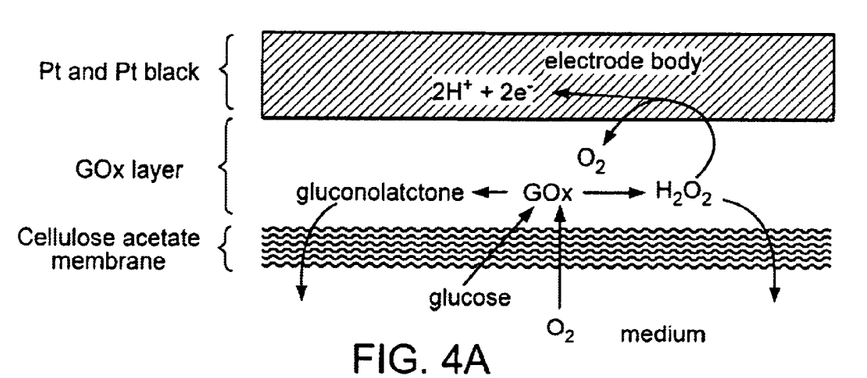
FIG. 4A is a schematic diagram showing chemical movements in and around a glucose sensor during glucose detection.

Prior to the present invention, those skilled in the art would have encountered several obstacles hindering the measurement of analyte flux with an enzyme-based electrode operating in self-referencing mode. One of these obstacles involves boundary artifacts, or distortions of flux measurements near the source. In a diffusion-determined environment, the depletion of an analyte such as glucose due to cellular consumption is highest near the cell surface and gradually decreases with increasing distance from the cell. Thus, as the analyte is consumed, $\Delta i$ should be negative because $i_{near}$ is less than $i_{far}$. However, actual glucose measurements have produced a positive value for $\Delta i$ in close proximity to cells, implying an improbable production of glucose. This phenomenon can be explained by considering the chemistry and limitations of the glucose sensor. As shown in FIG. 4A, in the presence of oxygen, glucose transported through the membrane is oxidized by glucose oxidase and converted to gluconolactone and hydrogen peroxide, which is oxidized at the electrode surface or diffused back into the medium. Restriction of the free movement of any of these analytes could impact sensor performance.

Figure 4B:
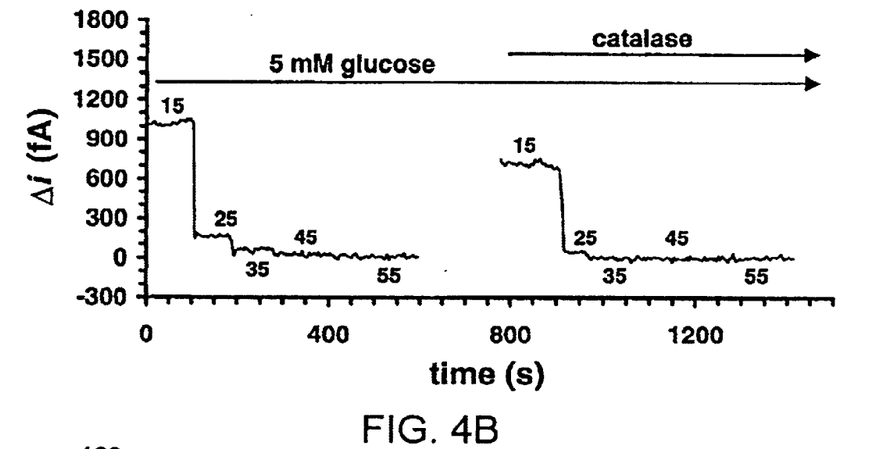
FIGS. 4B–C are graphs illustrating distortion in glucose measurements near a glass bead and amelioration of the distortion by catalase.
Figure 4C:
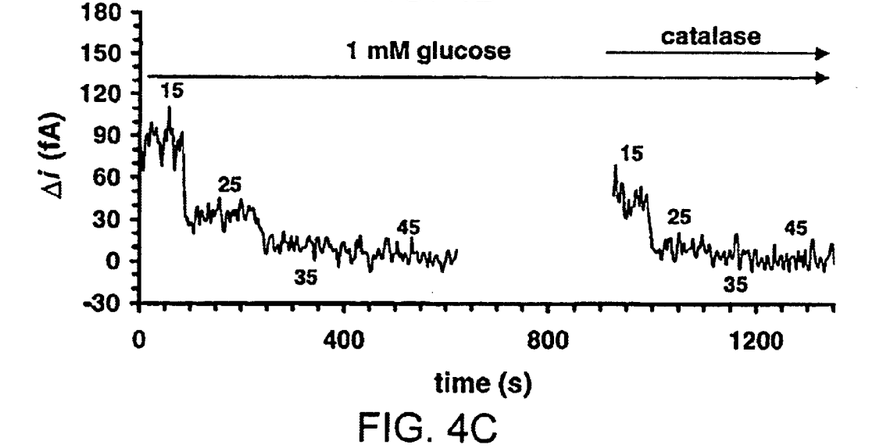

The present inventors investigated the above-referenced boundary effect using glass beads (50–80 μm diameter) to simulate a cell cluster. One of skill in the art might have anticipated that the presence of the bead could restrict both glucose and oxygen diffusion toward the sensor, such that $\Delta i$ would become more negative on approach, meaning the apparent glucose signal was smaller near the bead ($i_{near}$) than away from the bead ($i_{far}$). However, the opposite was observed. As shown in FIGS. 4B and 4C, a positive increase in $\Delta i$ was recorded as the sensor approached the bead surface. This indicates that the sensor signal was influenced more by distortion of hydrogen peroxide efflux from the sensor than by any interference from glucose or oxygen access. A comparison of FIGS. 4B and 4C indicates that the size of the boundary artifact is directly related to glucose concentration, as is the magnitude of the H$_2$O$_2$ production. The data shown are representative of nine measurements at 5 mM glucose (FIG. 4B) and five measurements at 1 mM glucose (FIG. 4C). The numbers near the traces indicate the mean location of the sensor relative to the glass bead in the self-referencing mode with a 20 μm excursion.

The glass bead may restrict hydrogen peroxide diffusion into the bulk while enhancing hydrogen peroxide diffusion back toward the electrode surface. This interpretation is supported by the effect of adding catalase (2000 units/ml), which encourages hydrogen peroxide to produce water and oxygen as follows:

$$2\ H_2O_2 \xrightarrow{Catalase} 2\ H_2O + O_2 \quad (7)$$

Wittstock et al., *Anal. Chem.* 69:5059–5066 (1997), disclose the use of catalase to "sharpen" the image of GOx activity obtained from a scanning electrochemical microscope. As shown in FIG. 4B, addition of catalase to a bulk medium with 5 mM glucose diminished the positive current recorded near the bead by about 30% during self-referencing. Thus, the use of catalase presents a method for reducing the boundary artifact. Although catalase does not eliminate the artifact, its presence allows glucose measurements at closer proximity to a biological target. It is unlikely that the presence of catalase in the medium will affect the biology of cell clusters, as catalase exists in the normal cell environment and is frequently added to cell cultures at similar concentrations to those described herein. As individual sensors may have different current output, the depth of the artifactual boundary layer is electrode-specific and each electrode should be assessed against a glass sphere prior to use.

Figure 5C:
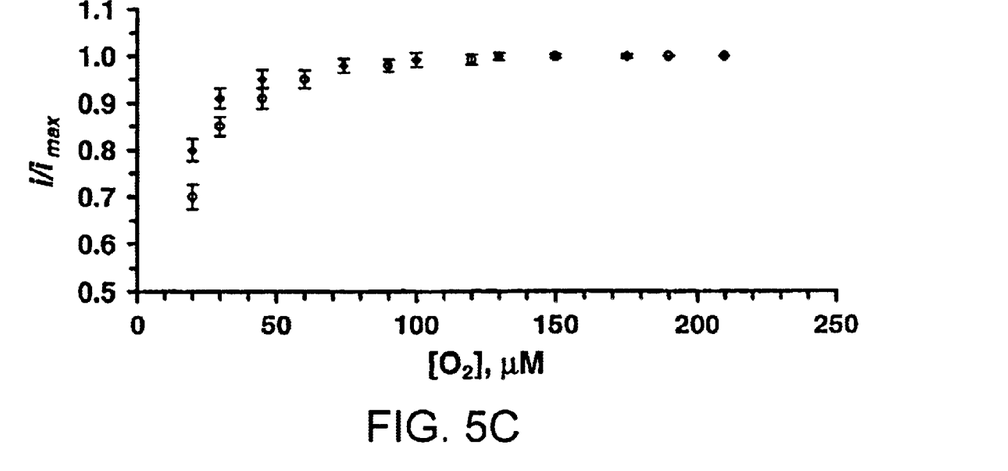
FIG. 5C is a graph showing the influence of oxygen on current response.
Figure 6A:
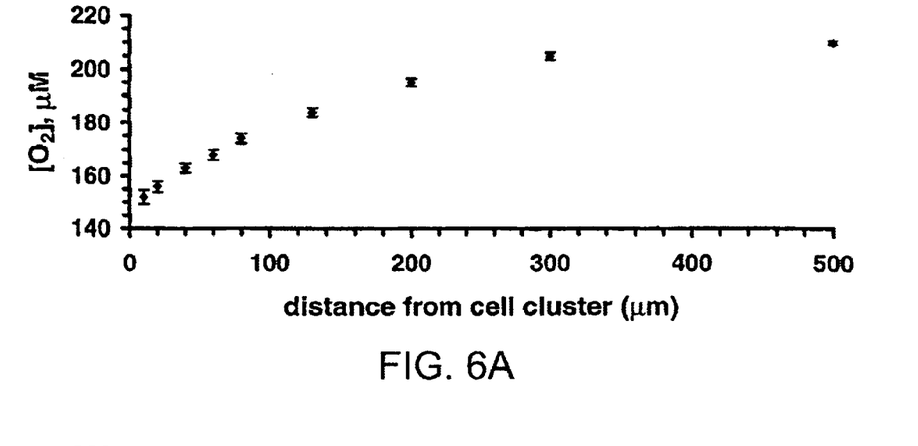
FIG. 6A is a graph showing the oxygen gradient around a cell cluster as measured by a stationary sensor.

Another obstacle to the use of a self-referencing enzyme-based electrode involves oxygen limitations. The mechanism of detection using oxidase enzymes involves oxygen (see, e.g., Equations (1) and (2)), and cells also consume oxygen. Therefore, knowledge of the oxygen gradient around cells is a prerequisite for accurate measurements of analyte flux with respect to those cells using an oxidase-based electrode. As illustrated in FIG. 5C, sensor signal is relatively independent of oxygen concentration for bulk oxygen concentrations above about 70 μM. An oxygen sensor operating in stationary mode was used to map the oxygen gradient in proximity to cell clusters with 5 mM glucose in the bulk medium, as shown in FIG. 6A. A clear oxygen gradient was evident, as expected for aerobically respiring cells. However, the dissolved oxygen concentration never fell below 140 μM, which is well above the 70 μM threshold for <5% error in the glucose sensor output. Subsequent glucose measurements should, therefore, be independent of changes in oxygen concentration.

Figure 6B:
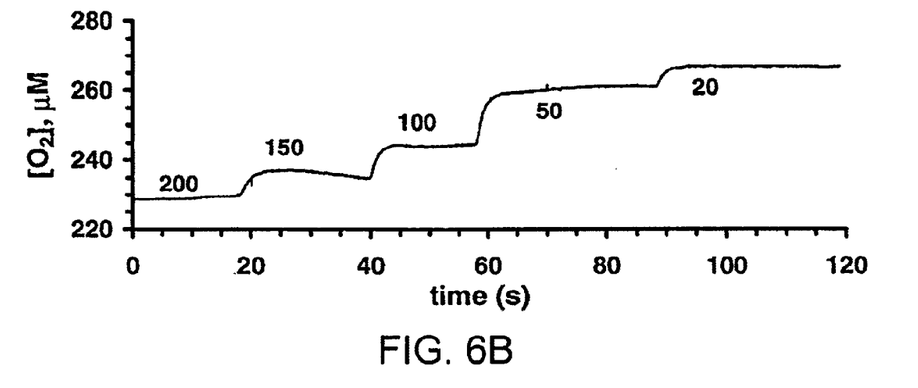
FIG. 6B is a graph showing the altered oxygen gradient around a cell cluster in the presence of an oxygen source as measured by a stationary sensor.
Figure 6C:
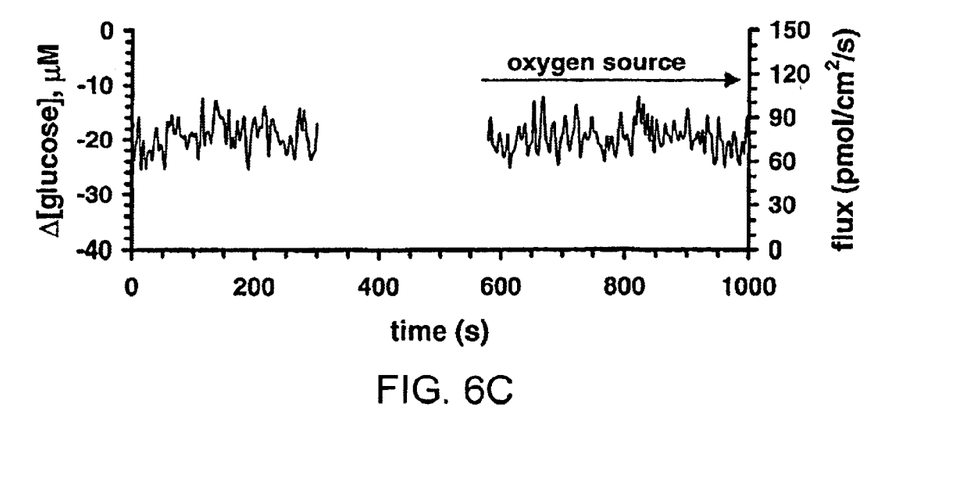
FIG. 6C is a graph showing glucose uptake measurements and their independence from the oxygen gradient when measured by a self-referencing microsensor of the present invention.

However, to further ensure that the apparent glucose signal is due to the glucose gradient and not the oxygen gradient, an oxygen source can be provided near the cell cluster to reverse the biological oxygen gradient. FIG. 6B shows the altered oxygen gradient around a cell cluster in the presence of an oxygen-diffusing pipette, measured in stationary mode. Oxygen levels are reversed in the presence of the oxygen source. However, as shown in FIG. 6C, glucose uptake by the β-cell cluster apparently is not affected by the presence of additional oxygen from the source. These observations confirm that glucose signal is not affected by oxygen fluctuation as long as the oxygen level remains above a certain threshold level, which varies depending on sensor linearity as disclosed by Zhang et al., *Anal. Chim. Acta* 281:513–520 (1993) and Jung et al., *J. Biol. Chem.* 275:6642–6650 (2000), the teachings of which are incorporated herein by reference. The glucose sensors described herein respond linearly up to 10 mM glucose; the 5 mM background glucose concentration used in the above-described experiments lies within this linearity region. At 5 mM glucose background, the glucose signal is affected less than 5% by oxygen concentration for oxygen concentrations above about 70 μM. As illustrated in FIG. 5C, oxygen influence increases as the background glucose concentration increases. Complete freedom from oxygen influence can be obtained by providing oxygen near the glucose sensor. The data cited here were generated using a 7 μm sensor, and results will vary with sensor diameter.

Since a glucose sensor is potentially sensitive to any oxidizable species, such as hydrogen peroxide, ascorbate, or urate, biological production of such species could produce signals open to misinterpretation. To test for potential oxidative interferences, an electrode fabricated in a manner identical to the glucose sensor but without glucose oxidase, was operated in the self-referencing mode. No signals were detected from four cell clusters under the conditions used to obtain the glucose consumption measurements with the glucose sensor. Thus, glucose measurements according to the invention can be assumed to be free of interference from extraneous oxidizable species.

V. Alternative Embodiments

As described above and demonstrated in the figures and the examples below, in some preferred embodiments the self-referencing microsensor of the present invention comprises glucose oxidase and is used to measure glucose flux. However, the microsensor of the invention can comprise any redox enzyme, and therefore can be used to measure the flux of a wide variety of molecules. The enzyme-based microsensor of the invention is useful for determining the flux of any analyte that is not itself electrochemically active, but is converted easily by a redox enzyme into another species that is readily detectable by an electrode. Suitable redox enzymes for use in electrodes of the invention include, without limitation, oxidases that act on and can therefore be used to detect, for example, lactate, galactose, glutamate and other amino acids, xanthine, or polyphenol; and dehydrdgenases. The electrochemically detectable species produced by oxidases is hydrogen peroxide; the electrochemically detectable species produced by dehydrogenases is the reduced form of the cofactor nicotinamide adenine dinucleotide (NADH). Further non-limiting examples of redox enzymes that can be used in electrodes of the invention include superoxide dismutase and peroxidase.

As described above and demonstrated in the figures and the examples below, in some preferred embodiments the self-referencing enzyme-based microsensors of the invention can be used to measure glucose flux with respect to artificial sources and/or pancreatic β-cells. However, those of skill in the art will understand that the systems and methods of the invention can be used to measure non-invasively and in real time the flux of a wide variety of analytes with respect to various artificial and biological sources. In some embodiments, the methods and systems of the invention can be used to assess the viability of an embryo by determining the flux of various analytes with respect to the embryo. Improved in vitro fertilization conditions have enabled longer culture periods of embryos, leading to the transfer of 8-cell and later stage embryos to patients. With long-term embryo culture, the potential exists to profile biochemical parameters in each embryo in order to select for transfer only embryos of good development potential. Prior to the present invention, such profiling and selection has been limited by the inherently small size of the sample available for assay. However, the small, sensitive, non-invasive self-referencing microsensors of the present invention now allow for the measurement of flux with respect to an embryo of various biologically significant molecules such as glucose. Since uptake of energy substrates is indicative of a healthy respiring embryo, these flux measurements allow for an assessment of the embryo's viability.

Other applications of the present invention include monitoring glucose transport from single cardiac myocytes or glutamate release by neurons, allowing correlation and analysis of mechanisms underlying normal and pathophysiologic conditions as related to heart function and disease or synaptic modulation and transmission. Measurement and comparison of flux levels for lactate and glucose from a single biological sample is another useful application of the invention. Such a comparison can be used to determine the balance between aerobic and anaerobic respiration in cells, as glucose is involved in aerobic metabolism while lactate is involved in anaerobic metabolism. As the present invention allows for sensitive flux measurements of a wide variety of analytes, the techniques of the invention also may be useful for the early detection of environmentally or medically hazardous chemicals spreading wrongfully or otherwise.

In still other embodiments, the methods of the present invention can be used to screen for biologically active compounds that affect the transmembrane flux of various molecules in cells. Flux of biologically significant analytes such as, for example, glucose, lactate, or glutamate, can be measured near cells in the absence and then in the presence of a test compound. A difference in flux measurements taken in the presence and in the absence of the test compound suggests that the test compound affects the flux of one or more biologically significant analytes, and therefore has biological activity and can be useful as a pharmaceutical product. In some embodiments, an array of multiple electrodes of the invention can be mounted on a single translational stage. Each electrode of the array comprises a different redox enzyme, thereby allowing for simultaneous determinations of flux for the multiple analytes acted upon by the various redox enzymes. Such an array of electrodes allows for efficient high-throughput screening for compounds that affect the biological flux of any one of a plurality of significant molecules.

The following nonlimiting examples further illustrate certain preferred embodiments of the present invention:

VI. EXAMPLES

Example 1

Fabrication of Glucose and Oxygen Ultramicrosensors

Glucose and oxygen microsensors were prepared as described by Jung et al., *J. Biol. Chem.* 275:6642–6650 (2000) and Jung et al., *Anal. Chem.* 71:3642–3649 (1999), with slight modification. Glucose microsensors were fabricated by gluing a platinum (Pt) wire 1.5 cm long and 25 μm in diameter (Johnson Matthey, Ward Hill, Mass.) into 25 gauge hypodermic tubing 5 cm long (Small Parts, Inc., Miami Lakes, Fla.) using silver epoxy from Epoxy Technology, Inc. (Billerica, Mass.). The wire was electrochemically etched down to ~4 μm diameter in an aqueous solution of 4 M KCN and 1 M NaOH by applying 4.0 V square waves for 8 min at a frequency of 250 Hz using a function generator (Leader Instruments, Hauppauge, N.Y.). The etched Pt wires were inserted into pulled glass capillaries (1.5 mm o.d.: TW 150-4, World Precision Instruments, Sarasota, Fla.) and filled with UV curable optical adhesive (Norland Products Inc., New Brunswick, N.J.) so that the etched wires protruded from the pipette tip by approximately 10 μm. The adhesive was cured under UV light for 20 min. The exposed Pt wires were etched again to form a cavity ~5

μm deep. Once etched, Pt particles were electrochemically plated on the recessed Pt wire at −0.2 V vs. Ag/AgCl in an aqueous solution of 10 mM hydrogen hexachloroplatinate (IV) hydrate (20,608–3: Aldrich, Milwaukee, Wis.) for 3–5 min. The amount of charge required for platinization was $1.2 \pm 0.3 \times 10^{-5}$ coulombs (n=26, mean±SD). Glucose oxidase (GOx: EC 1.1.3.4., type X-S from *Aspergillus niger*, Sigma, St. Louis, Mo.) was then loaded onto the platinum particles by immersing the tip of the electrodes in 1% (w/v) aqueous GOx solution for 10 min. The enzyme was immobilized with the vapor of 10% glutaraldehyde for 1 min. The immobilized enzyme layer was coated with 10% (w/v in acetone) 30 kD cellulose acetate by dipping for 10 s and drying for 60 s, repeated 4 times. All solutions were made up in distilled water (Milli-Q Plus: Millipore Co, Bedford, Mass.). The final tip diameter was ~8 μm.

Oxygen sensors were fabricated with platinum wires etched down to ~1 μm diameter, inserted into pulled glass capillaries with tip diameters of 3 μm, filled with optical adhesive, cured as above, and recessed by electro etching to form a cavity ~2 μm deep. The oxygen electrodes were then coated with 10% cellulose acetate. The final tip diameter was ~3 μm.

EXAMPLE 2

Testing of Glucose Microsensors

Calibration and measurement of the response times of sensors were performed in a solution of 50 mM HEPES buffer with 0.15 M NaCl at pH 7.4 at 37° C. by employing micro puffing (~4 μl/s) or a perfusion system (~32 μl/s). Glucose and oxygen sensors were polarized at +0.60 V and −0.60 V vs. Ag/AgCl reference electrodes, respectively. Sensors were conditioned for at least an hour in 5 mM glucose solutions. Sensors drifting in excess of ±5%/h were not employed for measurements. For the data presented herein, sensor drift was 2.8±1.8% in 30 min (mean±SD, n=16). FIG. 5 shows characterization data for glucose microsensors. Error bars represent one standard deviation.

A. Sensor Response Time

Figure 5A:
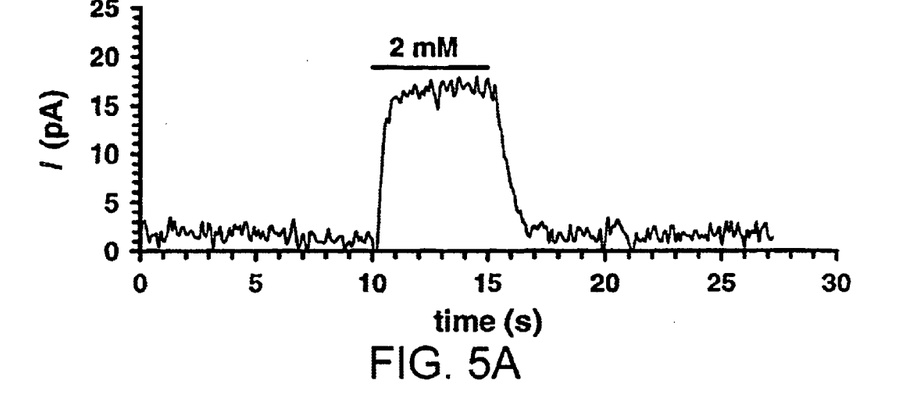
FIG. 5A is a graph of current versus time measured by a glucose microsensor.

FIG. 5A shows the current recorded during puffing a 2 mM glucose solution, with oxygen levels equilibrated to air, onto the sensor for 5 s. The sensor response time ($t_{90}$, time for signal change from 10% to 90% if maximum), measured in a steep gradient without translation or signal processing, was 0.46±0.07 s (n=6). This reflects an improvement over the response time of 5.2 s reported by Hu et al., *J. Neurochem.* 68:1745–1752 (1997), for a larger implantable glucose sensor with a cylindrical relative surface of 110 μm diameter and 500 μm length, with thick inner and outer membranes.

B. Calibration

Figure 5B:
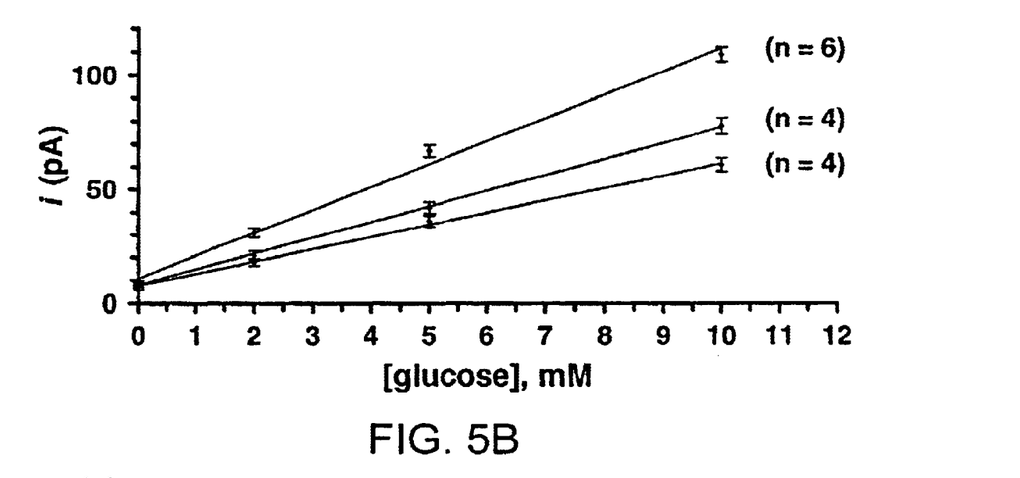
FIG. 5B is a graph showing the calibration of three different glucose microsensors.

FIG. 5B shows the calibration of three different glucose microsensors against known solutions of glucose. All of the measurements were performed in air-saturated buffer. The sensor response was linear up to 10 mM glucose, although slight deviations were observed for sensors exhibiting a high sensitivity. The average sensitivity of the sensors was 7.0±0.4 pA/mM (n=16).

C. Influence of Oxygen

The influence of oxygen on glucose microsensor performance was tested by measuring both glucose and oxygen with their respective sensors, while changing oxygen content in the perfused solution. Normal air saturated solutions containing 210 μM oxygen were deoxygenated by bubbling with argon gas. FIG. 5C shows the effect of oxygen concentration on glucose signal taken as the current at a given oxygen level (i) relative to that obtained at 210 μM ($i_{max}$). For 5 mM glucose (o), sensor signal was independent of oxygen concentration for oxygen concentrations above 148±5 μM (n=9). For 2 mM glucose (♦), oxygen limitations interfered less: freedom from oxygen influence was observed for oxygen concentrations above 97±4 μM (n=4).

EXAMPLE 3

Glucose Flux Measurements

A. Artificial Glucose Gradient

A glucose gradient was generated from a glass micropipette (tip diameter ~10 μm) holding a buffered solution of 500 mM or 99 mM glucose and 1 mM mannose in a 0.5% w/v agar solution. To prevent capillary movement of solution between the pipette and bath, agar was used and the source pipette was held in a closed volume micropipette holder (World Precision Instruments, Sarasota Fla.). To counter-balance the osmotic strength of the source pipette, a buffer solution with 500 mM mannose or 99 mM mannose with 1 mM glucose was used in the bath solution (volume of 4 ml). Mannose was not detected by the glucose sensor. The sensor was referenced to ground via a return 3M KCl and 3% agar bridge placed in the bulk medium. A gradient of glucose around the source pipette was allowed to establish for 30 min. Measurements within this gradient were made at several points by electrodes operating in stationary and self-referencing modes. In self-referencing mode, the glucose microsensor was laterally oscillated between two points 10 or 20 μm apart at a square wave frequency of 0.1, 0.15, 0.2 or 0.3 Hz.

Figure 3A:
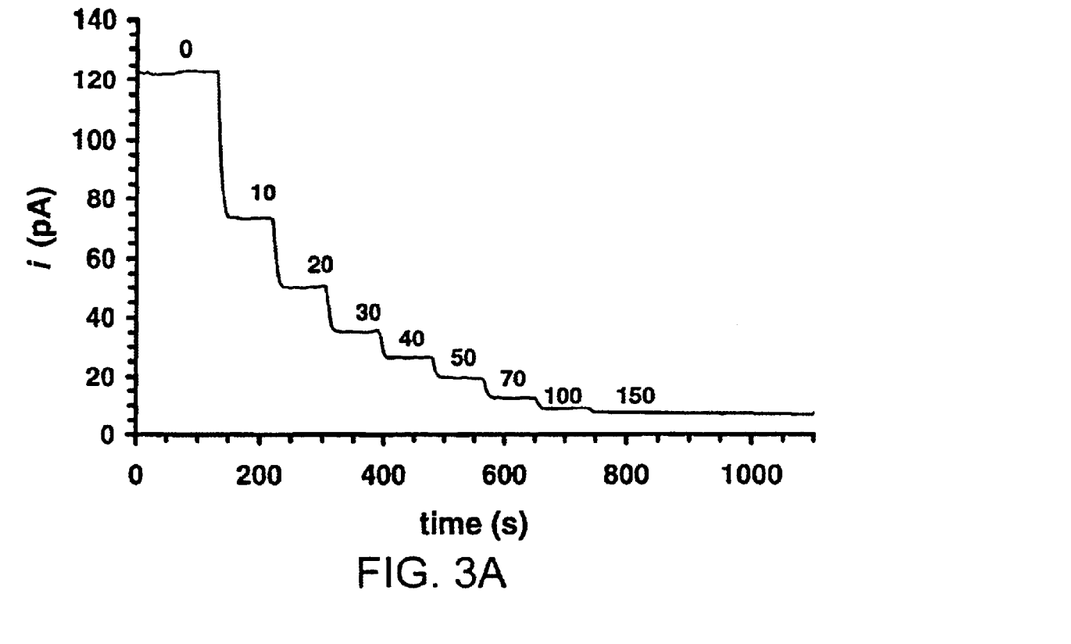
FIG. 3A is a real-time trace of a glucose gradient measured with a stationary glucose microsensor.
Figure 3B:
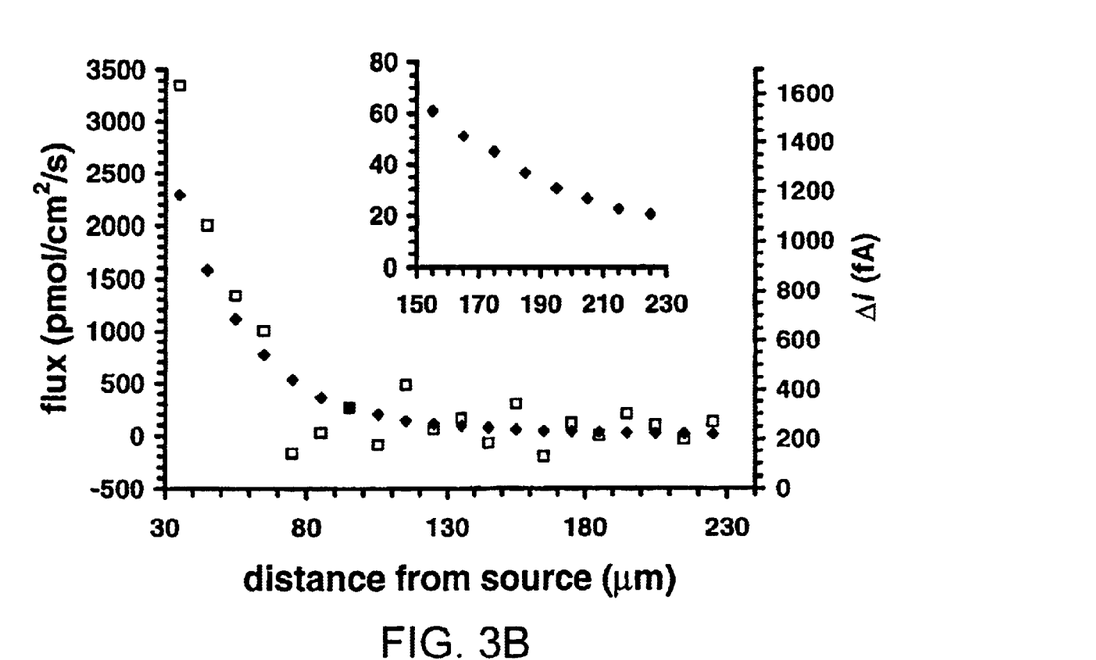
FIG. 3B is a graph comparing glucose flux values measured with a stationary sensor to glucose flux values measured with a self-referencing sensor of the present invention.

FIG. 3A is a real-time trace of the glucose gradient generated from a 500 mM glucose source, measured with the glucose microsensor in stationary mode. The numbers indicate the sensor locations from the source pipette. The trace demonstrates that the glucose sensor is suitable for gradient measurements. FIG. 3B shows glucose flux values from a 99 mM glucose source, measured with the glucose sensor in self-referencing mode with a 10 μm excursion at a frequency of 0.2 Hz (♦), or with the sensor held in stationary mode at both poles of translation (□). From these two stationary values a current difference can be calculated and flux determined. The sensor was repositioned in a sequence of 10 μm steps moving away from the source. In stationary mode (□), flux values smaller than 1 nmol $cm^{-2}$ $s^{-1}$ were hard to measure due to sensor drift and noise. However, in self-referencing mode, fluxes as low as 8.2±0.4 pmol $cm^{-2}$ $s^{-1}$ (n=7) were reliably measured. This flux value was derived from Δi of 9.8 fA. Values derived from stationary measurements could only follow the gradient within 70 μm of the source, after which point the values appear random. In contrast, the self-referencing data continued to follow the gradient even at distances in excess of 200 μm. These data illustrate the effectiveness of the self-referencing technique.

B. Glucose Consumption by Pancreatic β-Cells

1. Cell Culture

Pancreatic HIT cells donated from the laboratory of Dr. B. Corkey, Boston Medical Center, Boston University, were incubated in a culture medium composed of RPMI 1640 solution, 10 mM HEPES, 10% fetal bovine serum, 2 mM glutamine and 1% penicillin-streptomycin at 37° C. in humidified 95% air and 5% $CO_2$ and handled as described by Santerre et al., *Proc. Natl. Acad. Sci. USA* 78:4339–4343 (1981), the teachings of which are incorporated herein by reference. For trypsinization and splitting, trypsin-EDTA solution was added to a culture flask and incubated for 30 s while triturating with a transfer pipette. Serum was added to stop the digestive action of trypsin. Supernatant was removed after centrifugation at 1000 rpm for 2 min. Culture medium was added, and cells plated into glass bottom petri dishes (35 mm diameter, Matek, Ashland, Mass.) for incubation and subsequent observation. All cell culture media and solutions were from Gibco (Grand Island, N.Y.). All other chemicals were from Aldrich (Milwaukee, Wisc.) or Sigma Chemical Co. (St. Louis, Mo.).

Cell clusters, approximating to spheroids, appeared approximately two weeks after splitting. Their size ranged from 70 $\mu$m to 300 $\mu$m in diameter, depending on the time in culture.

2. Glucose Measurements

A glucose microsensor was positioned adjacent to the cluster and self-referenced perpendicularly to the contour of the expected glucose gradient. The glucose sensor was self-referenced at 0.2 Hz between 60 and 80 $\mu$m ($\Delta r$ of 20 $\mu$m) from the cluster surface to avoid $H_2O_2$ boundary artifacts. Flux measurements were done in HEPES-buffered solution containing 118 mM NaCl, 5.4 mM KCl, 2.4 mM $CaCl_2$, 1.2 mM $MgSO_4$, 1.2 mM $KH_2PO_4$, and 5 mM $NaHCO_3$. All measurements were made with 5 mM glucose in the medium. To ensure that the apparent glucose signal was due to the glucose gradient and not the oxygen gradient, oxygen was provided by a ~10 $\mu$m pipette located 10 $\mu$m from the cell cluster and approximately 50 $\mu$m from the glucose sensor to reverse the biological oxygen gradient. As shown in FIG. 6C, a clear glucose signal was detectable, indicating uptake by the cluster, and showed no change when the respiratory oxygen gradient was reversed. The trace shown in FIG. 6C is representative of data from five different clusters. In situ calibration of the sensor was performed immediately after the flux measurements. Data were only accepted if sensor drift was less than ±5% over the experimental period, which was typically 30 min. All data were reported as means ±SEM unless otherwise mentioned.

Applying Equations (5) and (6) above to measurements acquired from a total of nine cell clusters of 71 $\mu$m to 140 $\mu$m in diameter rendered a basal glucose consumption per unit volume of 61.7±9.5 fmol $nl^{-1}$ $s^{-1}$. This value is in agreement with the results of Freyer et al., *J. Cell. Physiol.* 124:516–524 (1985), who calculated a glucose consumption of ~48 fmol $nl^{-1}$ $s^{-1}$ at 5.5 mM glucose by EMT6/Ro mouse tumor cell clusters using an absorption measurement made at 340 nm with an enzyme reagent kit.

EXAMPLE 4

Pharmacological Manipulation of Glucose Consumption

A. FCCP

Figure 7A:
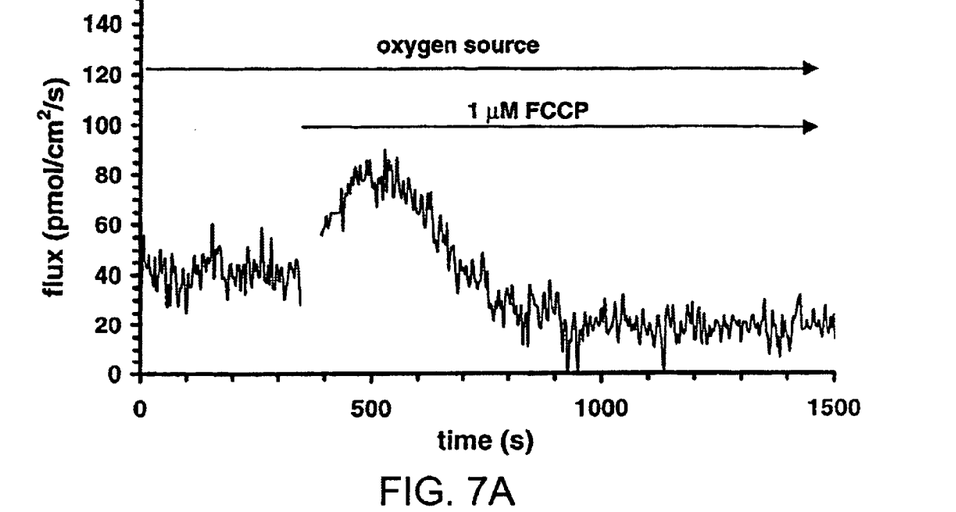
FIGS. 7A–B are graphs showing the influence of FCCP and rotenone, respectively, on glucose flux around a cell cluster as measured by a self-referencing microsensor of the present invention.

In the presence of an oxygen source, glucose consumption was modulated with the protonophore FCCP, (trifluoromethoxy carbonylcyanide phenylhydrazine), a compound known to increase oxygen consumption by depolarizing the mitochondrial membrane potential, increasing the rate of electron transfer and the consumption of NADH from the Krebs cycle and concomitant glucose consumption. FIG. 7A shows the effect of 1 $\mu$M FCCP on glucose flux around a cell cluster. The glucose sensor was self-referenced at 0.2 Hz between 60 and 80 $\mu$m ($\Delta r$ of 20 $\mu$m) from the cluster surface. The aliquot of FCCP was dropped on the meniscus of the medium to minimize disturbance of the existing glucose gradient. All measurements were performed with 5 mM glucose in the bath. The trace shown in FIG. 7A is representative of five different cluster measurements. Prior to FCCP introduction, a glucose influx of ~40 pmol $cm^{-2}$ $s^{-1}$ was obtained at 70 $\mu$m from the cluster. After introduction of FCCP as a 0.5 $\mu$l, 10 $\mu$M stock solution approximately 5 mm from the cluster, the glucose flux transiently increased and then decreased to below basal. The glucose flux initially increased by 93±16%, and subsequently fell after 3 min to 56±6% of the basal condition (n=5). The decrease in glucose consumption following the initial rise may be due to the deleterious effects of FCCP. The time lag seen in FIG. 7A includes the diffusion time for the FCCP to reach the cells after its application. Similar respiratory metabolic responses were observed for the oxygen sensor in the absence of the oxygen source. A control experiment confirmed that the glucose sensor performance was not affected by the presence of FCCP.

B. Rotenone

Figure 7B:
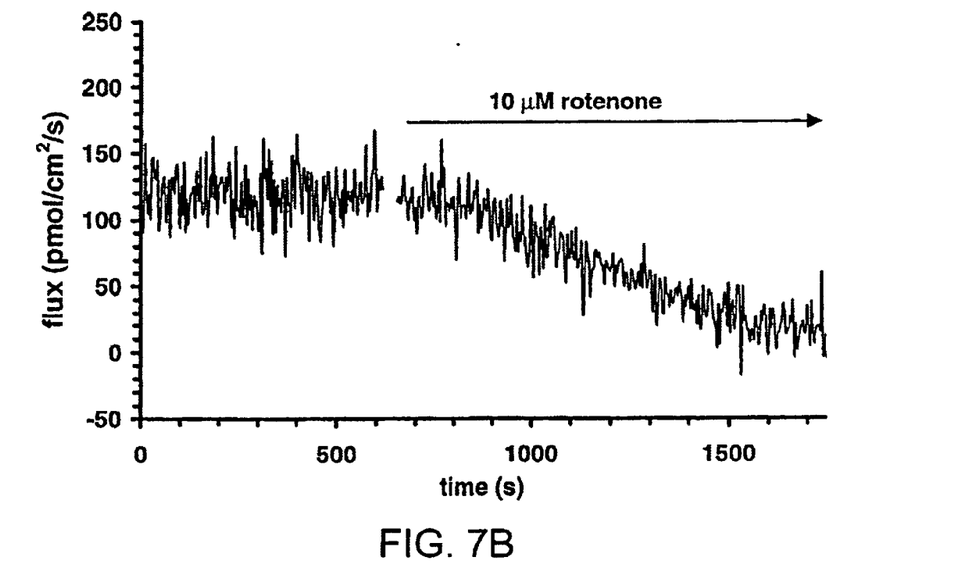

Glucose metabolism was further studied with rotenone, an inhibitor of NADH-dependent respiration in mitochondria. FIG. 7B shows the effect of 10 $\mu$M rotenone on glucose flux around a cell cluster. The glucose sensor was self-referenced at 0.2 Hz between 60 and 80 $\mu$m ($\Delta r$ of 20 $\mu$m) from the cluster surface. The rotenone aliquot was dropped on the meniscus of the medium to minimize disturbance of the existing glucose gradient. The measurement was performed with 5 mM glucose in the bath. The trace shown is representative of four different cluster measurements. Rotenone induced a 74±5% decrease in the level of glucose consumption after 10 min. A similar diffusion-related lag period between application and response was observed as for FCCP. During these experiments an abundant supply of oxygen was supplied by an artificial source positioned near the cluster. A control experiment confirmed that the glucose sensor performance was not affected by the presence of rotenone.

EXAMPLE 5

Non-Invasive Bioassay for Real-Time Measurement of Glucose Uptake by Single Embryos A carbon fiber electrode enclosed in a glass microcapillary was constructed with a diameter of approximately 10 $\mu$m. The fiber was electrochemically and chemically treated, enabling the attachment of biotin molecules to which avidin was subsequently bound. Biotinylated glucose oxidase was then bound to the avidin. Formation of $H_2O_2$ by glucose oxidase activity was measured amperometrically at 1.2 V. The glucose-sensitive electrode was connected to a head stage attached to a computer-controlled micromanipulator that oscillated the electrode between two points 30 $\mu$m apart and established self-referencing. The difference in concentration between the two points was applied to Fick's equation to calculate net glucose flux. A source micropipette of diameter 5–10 $\mu$m containing 200 mM glucose in 0.3% agar was used in a bath of 2 mM glucose to establish a gradient. The electrode measured the gradient and a net efflux from the source pipette. The electrode responded linearly to increasing glucose concentrations (0–35 mM).

Mouse 2-cell embryos were obtained from B6C3F1 crossed mice, and cultured in KSOM media to blastocyst stage. Blastocysts were placed in modified HTF with or without glucose, (5 mM) for glucose uptake measurement experiments. Measurement of glucose-dependent current adjacent to the zonae pellucidae of mouse blastocysts in the absence of glucose showed no net change in the current, indicating no net flux of glucose. However, in the presence of 5 mM glucose, the glucose-dependent current indicated a net glucose influx in 4 out of 7 blastocysts. The morphologic appearance of the blastocysts where no flux was detected was poor. Current indicating glucose influx in some mouse blastocysts is consistent with glucose metabolism by those cells. These results demonstrate the utility of self-referencing enzyme-based microsensors for assessing metabolism in single embryos in order to predict embryo viability.

EXAMPLE 6

Glutamate Measurements

Glutamate oxidase catalyzes the oxidative deamination of glutamate and produces hydrogen peroxide as a result of a two-electron equivalent reduction of oxygen according to the following reaction:

$$\text{glutamate} + O_2 \xrightarrow{\text{glutamate oxidase}} \text{glutamic acid} + NH_3 + H_2O_2 \qquad (8)$$

The production of hydrogen peroxide is detected electrochemically.

Figure 8:
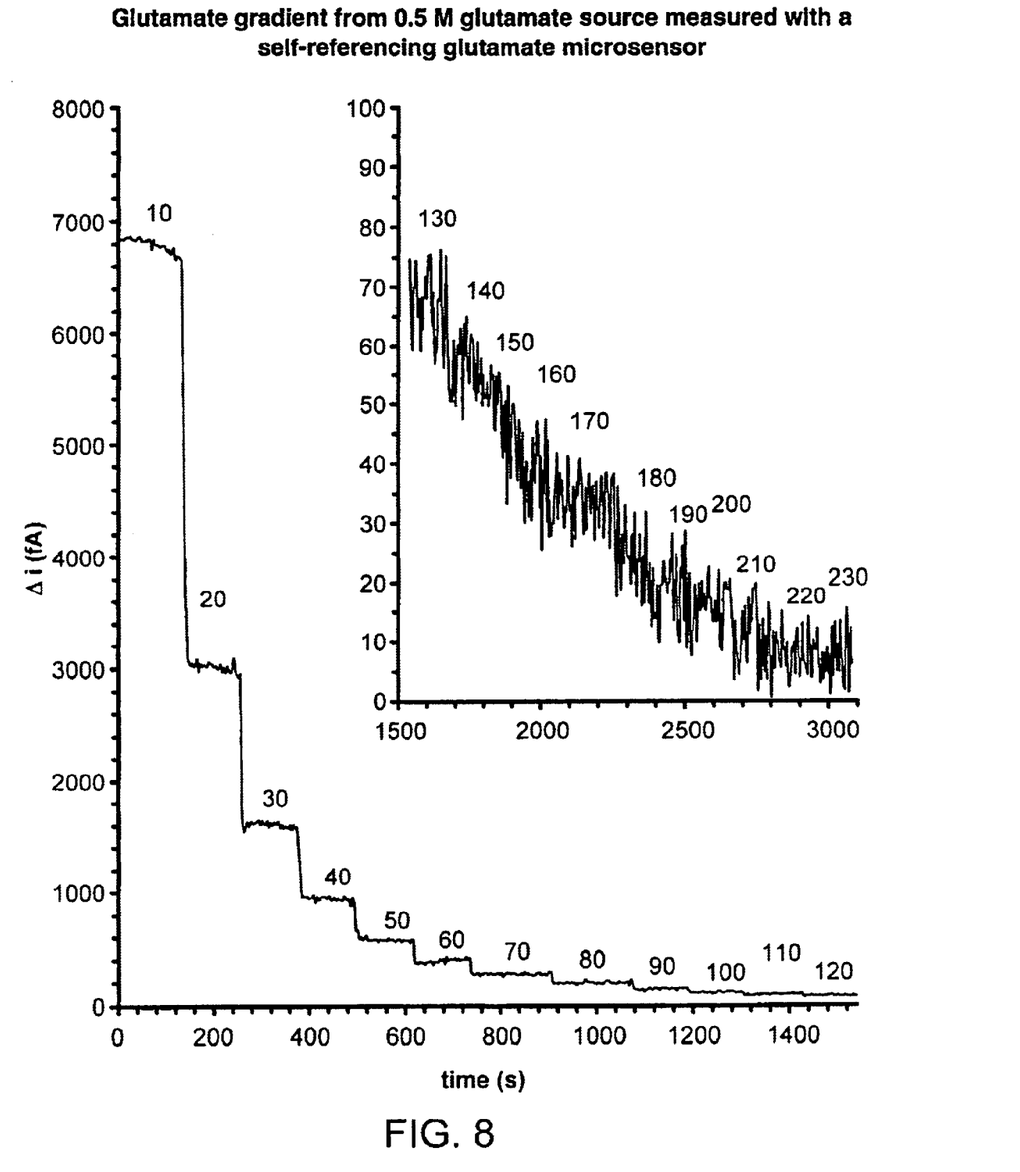
FIG. 8 is a graph showing a glutamate gradient measured by a self-referencing microsensor of the present invention.

FIG. 8 is a graph showing the glutamate gradient from a 0.5 M glutamate source measured with a self-referencing glutamate oxidase microsensor of the present invention. In the glutamate gradient, the glutamate microsensor was laterally oscillated in a square wave between two points 10 μm apart at a frequency of 0.2 Hz. As illustrated in FIG. 8, a difference current as low as about 7 fA was measured, corresponding to a flux of about 5 pmol/cm²/s. The results demonstrate that various oxidases can be utilized in the self-referencing electrodes of the invention.

What is claimed is:

1. A method of determining a flux of an analyte with respect to a source, the method comprising:
   (a) oscillating an electrode including an enzyme between first and second positions proximal to the source, whereby the enzyme contacts the analyte and generates a species detectable by the electrode, and whereby at each of the positions the concentration of the detectable species is dependent on the concentration of the analyte;
   (b) applying a voltage to a portion of the electrode so that the detectable species undergoes a chemical change to generate a position-dependent current;
   (c) sensing the current at the first and second positions; and
   (d) using the sensed currents to determine the flux of the analyte with respect to the source.

2. The method of claim 1, wherein the source comprises a mammalian cell.

3. The method of claim 1, wherein the enzyme is a dehydrogenase.

4. The method of claim 1, wherein the enzyme is an oxidase.

5. The method of claim 4, wherein the enzyme is glucose oxidase and the analyte is glucose.

6. The method of claim 4, wherein the enzyme is glutamate oxidase and the analyte is glutamate.

7. The method of claim 4, wherein the enzyme is lactate oxidase and the analyte is lactate.

8. The method of claim 1, further comprising providing oxygen to the source, thereby preventing distortion of the flux determination by oxygen depletion.

9. The method of claim 1, wherein the detectable species is hydrogen peroxide.

10. The method of claim 9, further comprising contacting the source with catalase, thereby preventing distortion of the flux determination near the source.

11. The method of claim 1, wherein the oscillating step includes moving the electrode at a frequency in the range of about 0.1 Hz to about 0.3 Hz.

12. The method of claim 1, wherein the distance between the first and second positions is between about 10 μm and about 50 μm.

13. The method of claim 1, wherein the first and second positions lie within a gradient of the analyte with respect to the source.

14. The method of claim 1, wherein the distance between a surface of the source and the midpoint between the first and second positions is between about 2 μm and about 500 μm.

15. A method of assessing the viability of an embryo by determining a flux of an analyte with respect to the embryo, the method comprising:
   (a) oscillating an electrode including an enzyme between first and second positions proximal to the embryo, whereby the enzyme contacts the analyte and generates a species detectable by the electrode, and whereby at each of the positions the concentration of the detectable species is dependent on the concentration of the analyte;
   (b) applying a voltage to a portion of the electrode so that the detectable species undergoes a chemical change to generate a position-dependent current;
   (c) sensing the current at the first and second positions;
   (d) using the sensed currents to determine the flux of the analyte with respect to the embryo; and
   (e) using the flux determination to assess the viability of the embryo.

16. A method of screening for compounds that affect a transmembrane flux of an analyte with respect to a cell, the method comprising:
   (a) oscillating an electrode including an enzyme between first and second positions proximal to the cell, whereby the enzyme contacts the analyte and generates a species detectable by the electrode, and whereby at each of the positions the concentration of the detectable species is dependent on the concentration of the analyte;
   (b) applying a voltage to a portion of the electrode so that the detectable species undergoes a chemical change to generate a position-dependent current;
   (c) sensing the current at the first and second positions;
   (d) using the sensed currents to determine the transmembrane flux of the analyte with respect to the cell;
   (e) contacting the cell with a test compound;
   (f) repeating steps (a) through (d) for the cell in the presence of the test compound; and
   (g) determining whether a difference exists between the transmembrane flux of the analyte with respect to the cell in the presence of the test compound and the transmembrane flux of the analyte with respect to the cell in the absence of the test compound, a difference indicating that the test compound affects the transmembrane flux of the analyte with respect to the cell.

* * * * *